(12) United States Patent
Lauchner et al.

(10) Patent No.: US 9,675,333 B2
(45) Date of Patent: Jun. 13, 2017

(54) CANNULA WITH FLEXIBLE HOLDER AND METHODS OF USE

(71) Applicant: KYPHON SARL, Neuchatel (CH)

(72) Inventors: Craig Lauchner, Mountain View, CA (US); Antonio Aaron Belton, Chicago, IL (US); Keith Aaron Grider, Chicago, IL (US)

(73) Assignee: Kyphon SÀRL, Neuchâtel (CH)

( * ) Notice: Subject to any disclaimer, the term of this patent is extended or adjusted under 35 U.S.C. 154(b) by 279 days.

(21) Appl. No.: 14/309,604

(22) Filed: Jun. 19, 2014

(65) Prior Publication Data

US 2015/0366548 A1    Dec. 24, 2015

(51) Int. Cl.
| | | |
|---|---|---|
| A61B 1/32 | (2006.01) | |
| A61B 17/02 | (2006.01) | |
| A61B 17/34 | (2006.01) | |
| A61B 90/30 | (2016.01) | |
| A61B 17/00 | (2006.01) | |
| A61B 17/70 | (2006.01) | |

(52) U.S. Cl.
CPC ...... *A61B 17/0218* (2013.01); *A61B 17/0293* (2013.01); *A61B 17/3421* (2013.01); *A61B 17/3423* (2013.01); *A61B 90/30* (2016.02); *A61B 17/3439* (2013.01); *A61B 17/7074* (2013.01); *A61B 2017/00477* (2013.01); *A61B 2017/00951* (2013.01); *A61B 2017/00991* (2013.01); *A61B 2017/346* (2013.01); *A61B 2017/3407* (2013.01); *A61B 2017/3433* (2013.01); *A61B 2017/3458* (2013.01); *A61B 2017/3492* (2013.01); *A61B 2090/309* (2016.02)

(58) Field of Classification Search
CPC ........... A61B 17/3415; A61B 17/3417; A61B 17/3423; A61B 17/3431; A61B 17/3439; A61M 25/02; A61M 2025/0206
USPC ......................... 600/214, 215, 216, 219, 224
See application file for complete search history.

(56) References Cited

U.S. PATENT DOCUMENTS

| | | | |
|---|---|---|---|
| 2,697,433 A | | 12/1954 | Zehnder |
| 4,397,647 A | * | 8/1983 | Gordon ................. A61M 25/02 |
| | | | 128/DIG. 26 |
| 4,484,913 A | * | 11/1984 | Swauger ................. A61M 5/00 |
| | | | 128/DIG. 26 |
| 4,608,977 A | | 9/1986 | Brown |
| 5,201,742 A | | 4/1993 | Hasson |
| 5,540,675 A | | 7/1996 | Hasson |
| 5,772,654 A | | 6/1998 | Leyva |

(Continued)

*Primary Examiner* — Anu Ramana (57) ABSTRACT

A surgical instrument includes a first member defining a passageway defining a first axis. A second member is positioned in the passageway and includes a lip extending at an angle relative to a second axis defined by the second member that engages a flange of the first member. A third member engages an outer surface of the first member. The third member includes an end surface. A fourth member defines a pathway having the first and second members disposed therein. The fourth member includes a first locking element. A fifth member includes a body including an inner surface that engages the third member. The fifth member includes a plurality of straps extending outwardly from the body. At least one of the straps includes a second locking element that engages the first locking element to fix the fourth member relative to the fifth member. Systems and methods are disclosed.

8 Claims, 8 Drawing Sheets

(56) References Cited

U.S. PATENT DOCUMENTS

| | | | |
|---|---|---|---|
| 5,785,648 A * | 7/1998 | Min | A61B 1/32 600/206 |
| 7,374,534 B2 * | 5/2008 | Dalton | A61B 17/0218 600/222 |
| 8,308,740 B2 | 11/2012 | Tolley et al. | |
| 8,361,091 B2 | 1/2013 | Schein et al. | |
| 8,500,759 B2 | 8/2013 | Koyfman et al. | |
| 8,603,078 B2 | 12/2013 | Stefanchik et al. | |
| 2006/0224044 A1 | 10/2006 | Marchek et al. | |
| 2009/0326462 A1 | 12/2009 | Wingardner, III et al. | |

* cited by examiner

CANNULA WITH FLEXIBLE HOLDER AND METHODS OF USE

TECHNICAL FIELD

The present disclosure generally relates to medical devices for the treatment of musculoskeletal disorders, and more particularly to a surgical system and method for accessing a surgical site to facilitate treatment.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. Surgical retractors may be employed during a surgical treatment to provide access and visualization of a surgical site. Such retractors space apart and support tissue and/or other anatomical structures to expose anatomical structures adjacent the surgical site and/or provide a surgical pathway to the surgical site. This disclosure describes an improvement over these prior art technologies.

SUMMARY

In one embodiment, a surgical instrument is provided. The surgical instrument comprises a first member comprising an inner surface defining a passageway defining a first longitudinal axis. The inner surface includes a flange extending perpendicular to the first longitudinal axis. A second member is positioned in the passageway and comprises a lip that engages the flange. The lip extends at an acute angle relative to a second longitudinal axis defined by the fourth member. A third member comprises an inner surface that engages an outer surface of the first member. The third member comprises an end surface. A fourth member comprises an inner surface defining a pathway having the first and second members disposed therein. The fourth member comprises a first locking element. A fifth member comprises a body including an inner surface that engages the third member. The fifth member comprises a plurality of straps extending outwardly from the body. At least one of the straps comprises a second locking element that engages the first locking element to fix the fourth member relative to the fifth member. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system and related methods of use disclosed are discussed in terms of medical devices for the treatment of musculoskeletal disorders and more particularly, in terms of a surgical system and method for accessing a surgical site to facilitate treatment. In one embodiment, the surgical system includes a surgical instrument, such as, for example, a cannula that reduces costs and provides unique features that address unmet needs. In some embodiments, the surgical instrument includes one or a plurality of light sources, such as, for example, light emitting diodes (LEDs) at a distal end of the surgical instrument for illuminating a patient's anatomy, thereby increasing effective visualization. In some embodiments, the surgical instrument includes light pipes for increasing effective visualization.

In some embodiments, the surgical instrument is configured for use by medical practitioners, such as, for example, interventionalists in connection with surgical procedures, such as, for example, decompression procedures. In some embodiments, the surgical instrument is configured for use in decompression procedures in which the patient remains conscious. During such procedures, surgical instruments are typically pushed dorsally as the patient's dorsal muscles contract, such as, for example, when the patient lifts his or her head. Accordingly, the disclosed surgical instrument is configured to remain stationary as a patient moves, thus avoiding unintended movement of the surgical instrument. In some embodiments, the surgical instrument creates an anchor by a ring that attaches to the patient with, for example, adhesives or by tape strips. In some embodiments, the ring is elastomeric. A cannula top comprises straps that attach to the elastomeric ring. In some embodiments, the straps include cutouts configured for disposal of projections extending from the ring. When the projections are disposed in the cutouts, the straps are fixed relative to the ring. In some embodiments, the ring includes a plurality of spaced apart projections disposed circumferentially about the ring and the straps each include a plurality of cutouts that are spaced apart along the length of each strap. This configuration allows a medical practitioner to pull or wag the cannula into a desired position, for example, and hold the cannula in the desired position by inserting at least one of the projections into at least one of the cutouts. Holding the instrument in place prevents the need to reposition the instrument in response to patient movement as well as the need to control fresh bleeding. In some embodiments, the wag and hold feature allows the medical practitioner to free their off-hand.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" am relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and methods of employing the surgical system in accordance with the principles of the present disclosure. Alternate embodiments are also disclosed. Reference will now be made in detail to the exemplary embodiments of the present disclosure, which are illustrated in the accompanying figures. Turning to FIGS. 1-20, there are illustrated components of a surgical system 20 including a surgical instrument, such as, for example, a retractor or cannula 22, in accordance with the principles of the present disclosure.

The components of surgical system 20 can be fabricated from biologically acceptable materials suitable for medical applications, including metals, synthetic polymers, ceramics and bone material and/or their composites, depending on the particular application and/or preference of a medical practitioner. For example, the components of surgical system 20, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of surgical system 20 may have material composites, including the above materials, to achieve various desired characteristics such as strength, rigidity, elasticity, compliance, biomechanical performance, durability and radiolucency or imaging preference. The components of surgical system 20, individually or collectively, may also be fabricated from a heterogeneous material such as a combination of two or more of the above-described materials. The components of surgical system 20 may be monolithically formed, integrally connected or include fastening elements and/or instruments, as described herein.

Cannula 22 includes a first member 24 extending along a longitudinal axis A between an end 26 and an opposite end 28. End 26 comprises a flange 30 extending perpendicular to axis A. Member 24 comprises an inner surface 32 that is concavely curved between axial surfaces 34, 36 of member 24. Surface 32 defines a passageway 38 having a semi circular cross sectional configuration. Flange 30 defines an opening 40 extending through flange 30. Opening 40 is in communication with passageway 38. Surface 32 comprises a concavely curved recess 42 configured for disposal of a protrusion 44 of a second member 46 to provisionally fix member 24 relative to member 46, as will be discussed. In some embodiments, member 24 comprises a first recess 42 adjacent surface 34 and a second recess 42 adjacent surface 36. In some embodiments, member 24 comprises one or a plurality of recesses 42. End 26 comprises an outer surface including an external thread form 48 configured to engage an internal thread form 50 of a top nut, such as, for example, a third member 52.

Figure 9:
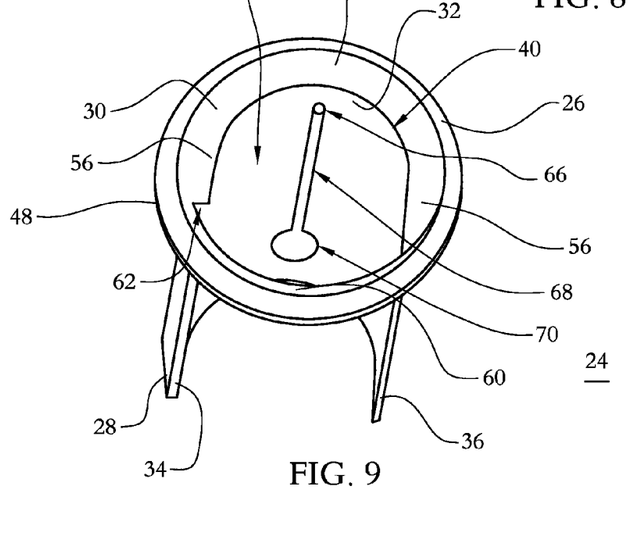
FIG. 9 is a top, perspective view of a component shown in FIG. 1.
Figure 10:
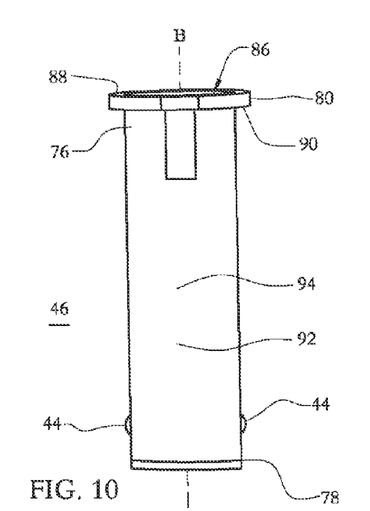
FIG. 10 is a perspective view of a component shown in FIG. 1.

In some embodiments, flange 30 includes an arcuate portion 54 extending between planar or linear portions 56 of flange 30. Portion 54 is concave and is continuously curved between portions 56. Portions 56 extends parallel to one another and are configured to engage outer surfaces of planar side walls 58 of member 46, as will be discussed. In some embodiments, end 26 includes an arcuate surface 60 opposite portion 54. Surface 60 is concave and is continuously curved. In some embodiments, end 26 includes an indent 62 at an interface between surface and one of portions 56, as shown in FIG. 9. In some embodiments, indent 62 facilitates assembly of cannula 22.

In some embodiments, recesses 42 are hemispherical. In some embodiments, all or only a portion of each recess 42 may be variously configured and dimensioned, such as, for example, planar, concave, polygonal, irregular, uniform, non-uniform, staggered, tapered, consistent or variable. In some embodiments, member 24 can be variously connected with member 46, such as, for example, monolithic, integral connection, frictional engagement, threaded engagement, mutual grooves, screws, adhesive, nails, barbs and/or raised element. In some embodiments, passageway 38, opening 40, recess 42 and/or protrusion 44 may have various cross section configurations, such as, for example, oval, oblong, triangular, rectangular, square, polygonal, irregular, uniform, non-uniform, variable, tubular and/or tapered. In some embodiments, flange 30 may be disposed at alternate orientations, relative to axis A, such as, for example, transverse, perpendicular and/or other angular orientations such as acute or obtuse, co-axial and/or may be offset or staggered. In some embodiments, recess 42 and/or protrusion 44 may have various surface configurations, such as, for example, smooth and/or surface configurations to enhance fixation, such as, for example, rough, arcuate, undulating, porous, semi-porous, dimpled, polished and/or textured according to the requirements of a particular application. In some embodiments, member 24 is made entirely from molded plastic.

Figure 7:
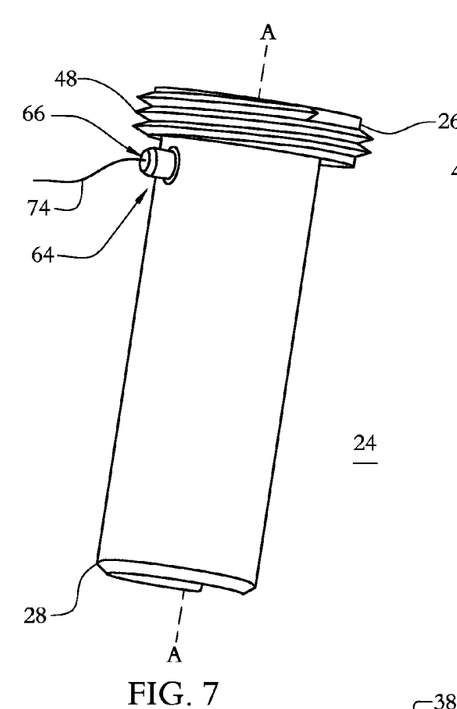
FIG. 7 is a perspective view of a component shown in FIG. 1.
Figure 8:
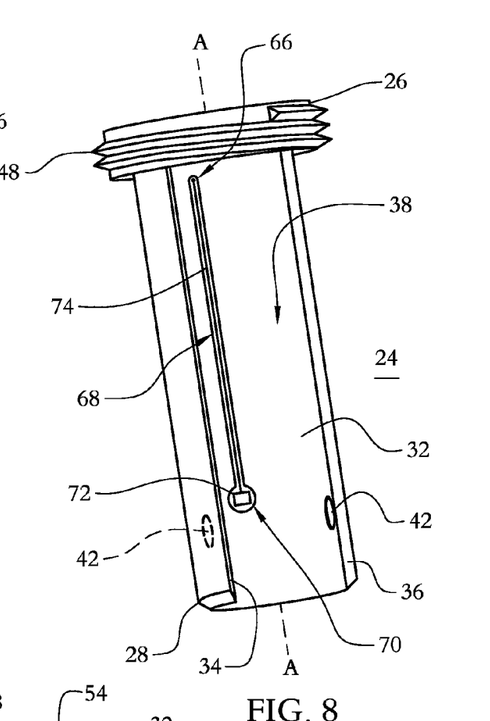
FIG. 8 is a perspective view of a component shown in FIG. 1.

In some embodiments, the outer surface of member 24 comprises a port 64 including an opening 66 that is in communication with a lumen 68 defined by surface 32. Lumen 88 terminates in a cavity 70 that extends into surface 32 without extending through the outer surface of member 24, as shown in FIGS. 8 and 9. Lumen 68 also extends into surface 32 without extending through the outer surface of member 24, as shown in FIGS. 8 and 9. In some embodiments, lumen 68 does not extend through surface 32 or the outer surface of member 32 such that lumen 68 is embedded within a wall thickness of member 24, and is thus concealed from view. A light source 72 such as, for example, a light emitting diode (LED) is positioned in cavity 70 such that a wire 74 connected to light source 72 extends through opening 66 and port 64, as shown in FIG. 7. In some embodiments, wire 74 is used to provide power to light source 72. Light source 72 is configured to illuminate at least a portion of passageway 38. In some embodiments, light source 72 is embedded within member 24 such that light source 72 is permanently fixed to member 24. In some embodiments, light source 72 is embedded within member 24 and at least a portion of member 24 is transparent or translucent to allow tight from light source 72 to pass through member 24. In some embodiments, cannula 22 includes a battery configured to power light source 72.

Member 48 extends along a longitudinal axis B between an end 76 and an opposite end 78. End 76 comprises a lip 78 extending at an angle 82 relative to axis B. Lip 80 includes an inner surface 84 defining an opening 86. Lip 80 includes planar upper and lower surfaces 88, 90 that extend parallel to one another. Member 46 includes an arcuate wall 92 that extends between opposite planar side walls 58. Wall 92 includes an outer surface 94 that is convexly curved between walls 58 and an inner surface opposite surface 94 that is concavely curved between walls 58. In some embodiments, surface 94 is configured to engage surface 60 when member 46 is positioned in passageway 38. In some embodiments, surface 94 and surface 60 each have a smooth or even configuration to allow surface 94 to slide along surface 60. Outer surfaces of walls 58 each include a protrusion 44 extending outwardly therefrom. Protrusions 44 are positioned adjacent end 78 and are convexly curved. Surface 84 and inner surfaces of walls 58, 92 define a conduit 96.

In some embodiments, protrusions 44 each have a hemispherical configuration that matches that of recesses 42. In some embodiments, protrusions 44 are aligned and/or coaxial. In some embodiments, protrusions 44 are made from a material that is different from a material the remaining portions of member 46 are made. In some embodiments, protrusions 44 are made from a material that is more flexible and/or deformable than a material the remaining portions of member 46 are made. In some embodiments, protrusions 44 are made from a material that is more rigid than a material the remaining portions of member 46 are made. In some embodiments, cannula 22 is made entirely radiopaque materials to aid in fluoroscopic visualization. In some embodiments, member 46 is radiopaque to aid in fluoroscopic visualization. In some embodiments, only a distal tip of member 46 is radiopaque to aid in fluoroscopic visualization. In some embodiments, member 46 is made entirely from molded plastic.

In some embodiments, the inner surface of wall 92 is continuously curved between walls 58 and surface 94 is continuously curved between walls 58. In some embodiments, angle 82 is an acute angle. In some embodiments, angle 82 is an angle between about 45 and about 90 degrees. In some embodiments, lip 80 may be disposed at alternate orientations, relative to axis 8, such as, for example, transverse, perpendicular and/or other angular orientations such as acute or obtuse, co-axial and/or may be offset or staggered. In some embodiments, opening 86 may have various cross section configurations, such as, for example, circular, oval, oblong, triangular, rectangular, square, polygonal, irregular, uniform, non-uniform, variable, tubular and/or tapered. In some embodiments, all or only a portion of protrusions 44, walls 58 and/or the wall 92 may be variously configured and dimensioned, such as, for example, planar, concave, polygonal, irregular, uniform, non-uniform, staggered, tapered, consistent or variable.

Figure 11:
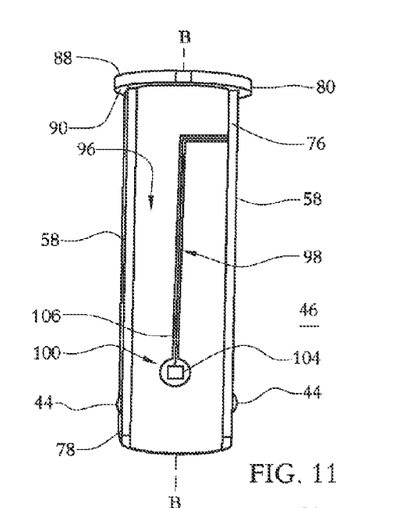
FIG. 11 is a perspective view of a component shown in FIG. 1.
Figure 12:
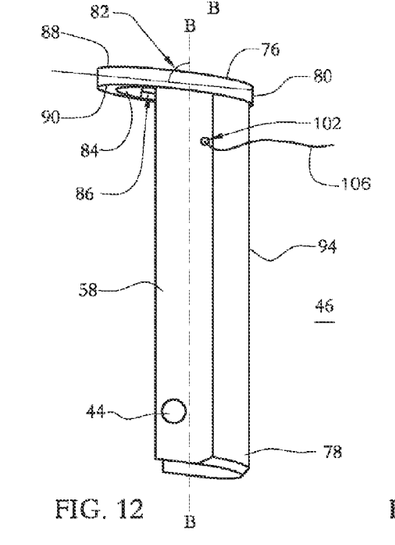
FIG. 12 is a perspective view of a component shown in FIG. 1.
Figure 13:
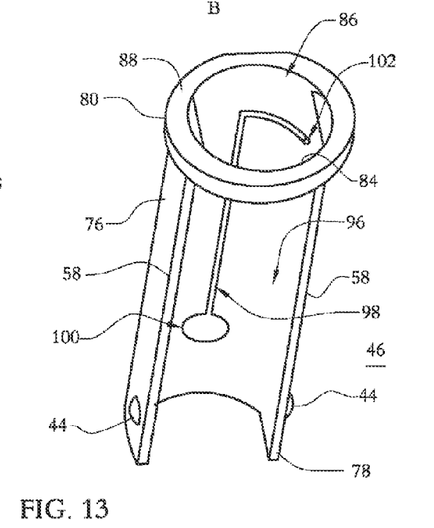
FIG. 13 is a perspective view of a component shown in FIG. 1.
Figure 14:
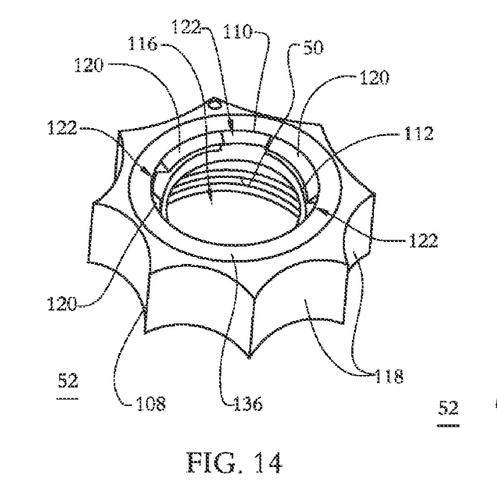
FIG. 14 is a top, perspective view of a component shown in FIG. 1.
Figure 15:
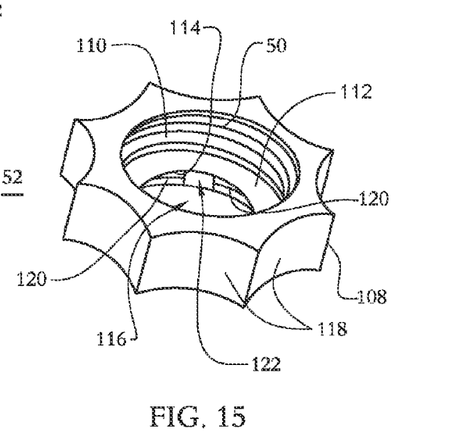
FIG. 15 is a bottom, perspective view of a component shown in FIG. 1.
Figure 16:
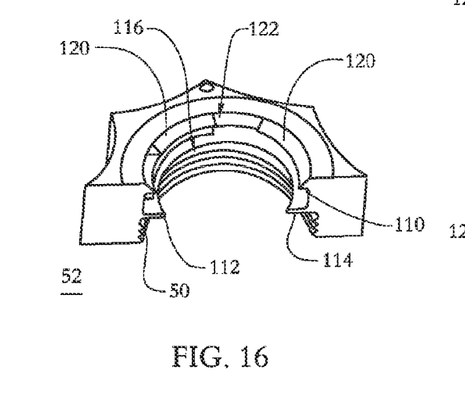
FIG. 16 is a perspective, cross sectional view of a component shown in FIG. 1.
Figure 17:
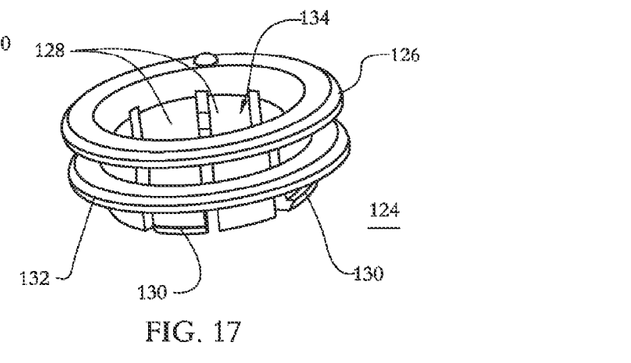
FIG. 17 is a perspective view of a component shown in FIG. 1.

In some embodiments, the inner surface of wall 92 comprises a lumen 98 that terminates in a cavity 100 that extends into the inner surface of wall 92 without extending through surface 94, as shown in FIGS. 11 and 13. Lumen 98 includes a first portion extending transverse or perpendicular to axis B and a second portion extending parallel to axis B. Cavity 100 is in communication with the second portion of lumen 98. The first and second portions of lumen 98 are configured to position cavity 100 equidistant between walls 58. Lumen 98 is in communication with an aperture 102 extending through inner and outer surfaces of one of walls 110. Lumen 98 also extends into the inner surface of wall 92 without extending through surface 94, as shown in FIGS. 11 and 13. In some embodiments, lumen 98 does not extend through the inner surfaces of walls 92, 58 such that lumen 98 is embedded within a wall thickness of walls 92, 58, and is thus concealed from view. A light source 104, such as, for example, a light emitting diode (LED) is positioned in cavity 100 such that a wire 106 connected to light source 104 extends through lumen 98 and aperture 102, as shown in FIGS. 11 and 12. In some embodiments, wire 106 is used to provide power to light source 104. Light source 104 is configured to illuminate at least a portion of conduit 96. In some embodiments, light source 104 is embedded within member 46 such that light source 104 is permanently fixed to member 46. In some embodiments, light source 104 is embedded within member 46 and at least a portion of member 46 is transparent or translucent to allow light from light source 104 to pass through member 46. In some embodiments, cannula 22 includes a battery configured to power light source 104.

Member 52 comprises a body 26 including an inner surface 28 having an annular projection 112 extending inwardly therefrom. A bottom surface of projection 112 defines an end surface 114 of member 52. Surface 114 extends perpendicular to a longitudinal axis defined by member 52. Surface 114 has a smooth or even configuration configured to engage surface 88, as will be discussed. An inner surface of projection 112 defines a throughhole 116 having a circular cross sectional configuration. In some embodiments, throughhole 116 may have various cross section configurations, such as, for example, oval, oblong, triangular, rectangular, square, polygonal, irregular, uniform, non-uniform, variable, tubular and/or tapered. In some embodiments, member 24 can be variously connected with member 52, such as, for example, monolithic, integral connection, frictional engagement, threaded engagement, mutual grooves, screws, adhesive, nails, barbs and/or raised element. In some embodiments, an outer surface of member 52 opposite surface 110 includes a plurality of spaced apart projections defining notches 118 therebetween configured for gripping by a medical practitioner. In some embodiments, notches 118 are concavely curved between adjacent projections. In some embodiments, the outer surface of member 52 may have various surface configurations to enhance gripping thereof, such as, for example, rough, arcuate, undulating, porous, semi-porous, dimpled, polished and/or textured. In some embodiments, all or only a portion of notches 118 may be variously configured and dimensioned, such as, for example, planar, concave, polygonal, irregular, uniform, non-uniform, staggered, tapered, consistent or variable. In some embodiments, body 108 and/or member 52 is made entirely from molded plastic.

Member 52 includes a first portion on a proximal side of projection 112 and a second portion on a distal side of projection 112. The second portion of member 52 includes thread form 50 that engages thread form 48 to couple member 52 with member 24. The first portion of member 52 includes an extension 120 extending inwardly from surface 110. Extension 120 is separated into a plurality of sections by a plurality of gaps 122. Member 52 comprises a snap-in ring 124 removably disposed in body 108. Snap-in ring 124 comprises an annular band 126 and a plurality of spaced apart fingers 128 extending from band 126. In some embodiments, at least one of fingers 128 includes an outward facing extension 130 at a distal tip thereof. In some embodiments, every other finger 128 includes extension 130 such that a finger 128 that includes extension 130 is not positioned directly adjacent another finger 128 that includes extension 130. Extensions 130 are configured to engage extension 120 to prevent axial translation of snap-in ring 124 relative to body 108. In some embodiments, snap-in ring 124 is inserted into body 108 such that extensions 130 are aligned with gaps 122. Snap-in ring 124 is translated relative to body 108 in the direction shown by arrow C until extensions 130 are positioned distal to extension 120. Snap-in ring 124 is rotated in a first direction, such as, for example, clockwise or counterclockwise such that extensions 130 are positioned between extension 120 and projection 112 to prevent snap-in ring 124 from moving relative to body 108 in the directions shown by arrows C and D. In some embodiments, fingers 128 are deformable such that snap-in ring 124 can be inserted into body 108 such that extensions 130 are aligned with extensions 120. Snap-in ring 124 is translated relative to body 108 in the direction shown by arrow C until extensions 130 engage extension 120. Snap-in ring 124 is further translated in the direction shown by arrow C such that fingers 128 deflect inwardly to move extensions 130 over extension 120 such extensions 130 are positioned between extension 120 and projection 112 to prevent snap-in ring 124 from moving relative to body 108 in the directions shown by arrow D. In some embodiments, fingers 128 are resiliently biased outwardly. In some embodiments, snap-in ring 124 is made entirely from molded plastic. In some embodiments, outer surfaces of extensions 130 are beveled to facilitate extensions 130 moving over extension 120 as extensions 130 deflect inwardly, as discussed above.

Figure 3:
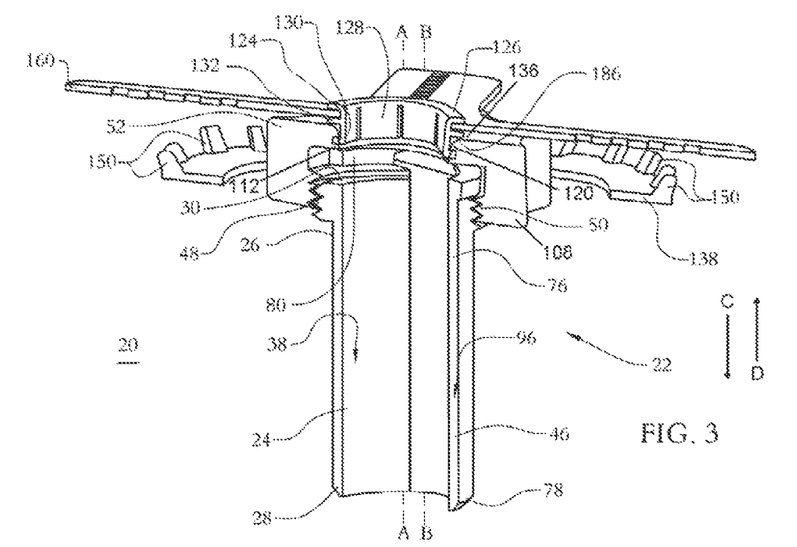
FIG. 3 is a perspective, cross sectional view of components shown in FIG. 1.
Figure 4:
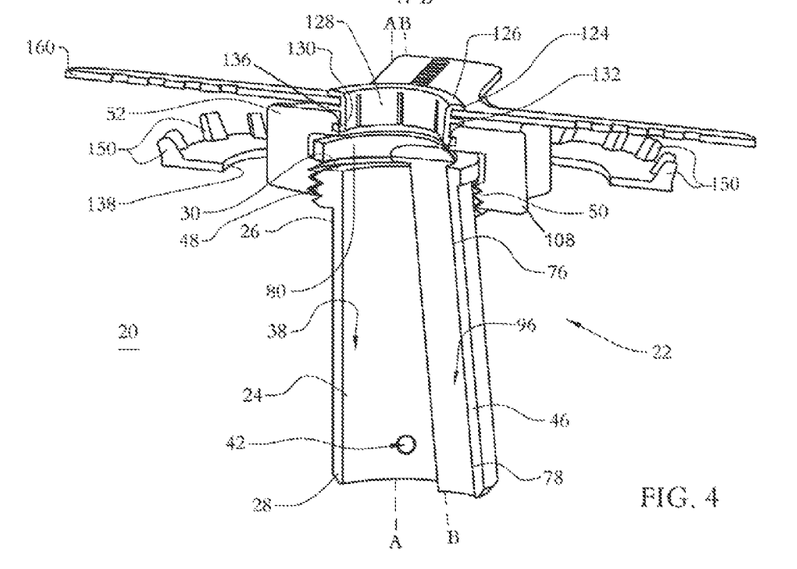
FIG. 4 is a perspective, cross sectional view of components shown in FIG. 1.

In some embodiments, snap-in ring 124 comprises an annular band 132 positioned between band 126 and extensions 130 such that band 132 surrounds fingers 128 to prevent fingers 128 from deflecting outwardly passed band 132. An inner surface of snap-in ring 124 defines a channel 134 having a circular cross sectional configuration that is coaxial with throughhole 116. In some embodiments, channel 134 may have various cross section configurations, such as, for example, oval, oblong, triangular, rectangular, square, polygonal, irregular, uniform, non-uniform, variable, tubular and/or tapered. In some embodiments, band 132 has a maximum diameter that is greater than that of an opening in body 108 such that band 132 engages an upper surface 136 of body 108, as shown in FIGS. 3 and 4, for example. In some embodiments, band 132 has an arcuate configuration and surface 136 is beveled inwardly toward throughhole 116 to accommodate the arcuate configuration of band 132.

Figure 5:
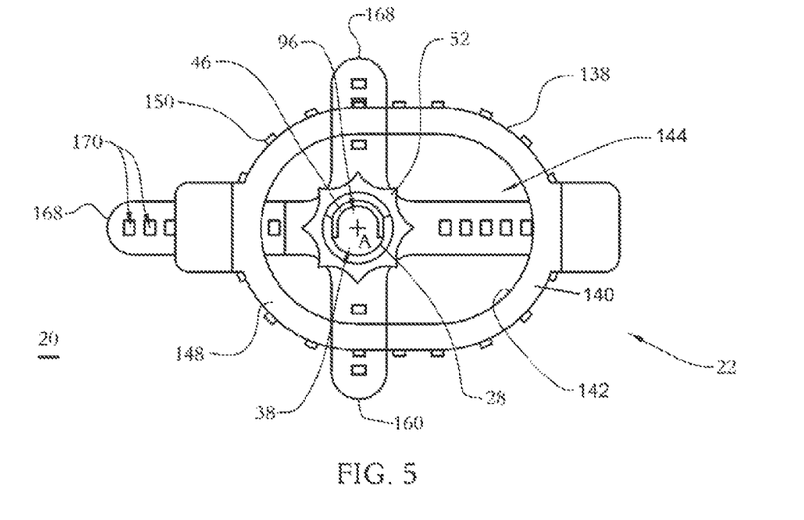
FIG. 5 is a bottom view of components shown in FIG. 1.
Figure 6:
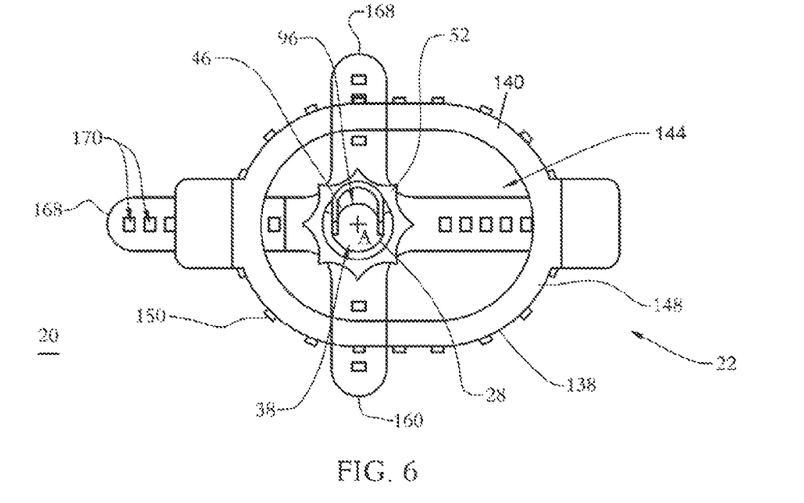
FIG. 6 is a bottom view of components shown in FIG. 1.
Figure 18:
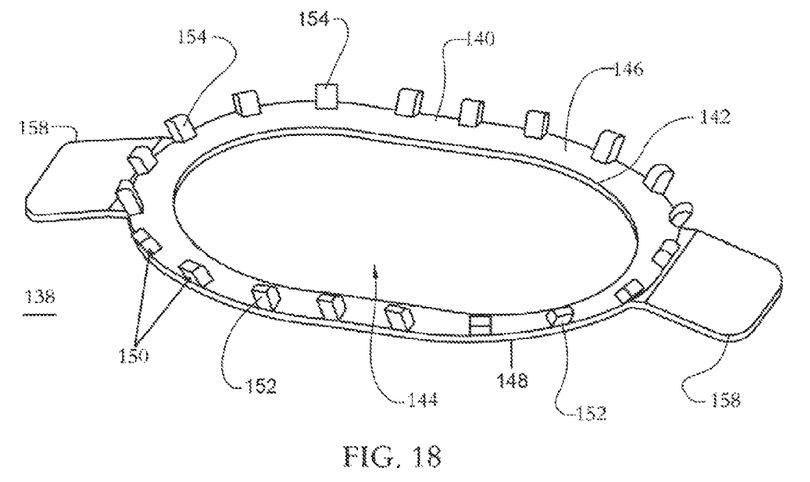
FIG. 18 is a perspective view of a component shown in FIG. 1.
Figure 20:
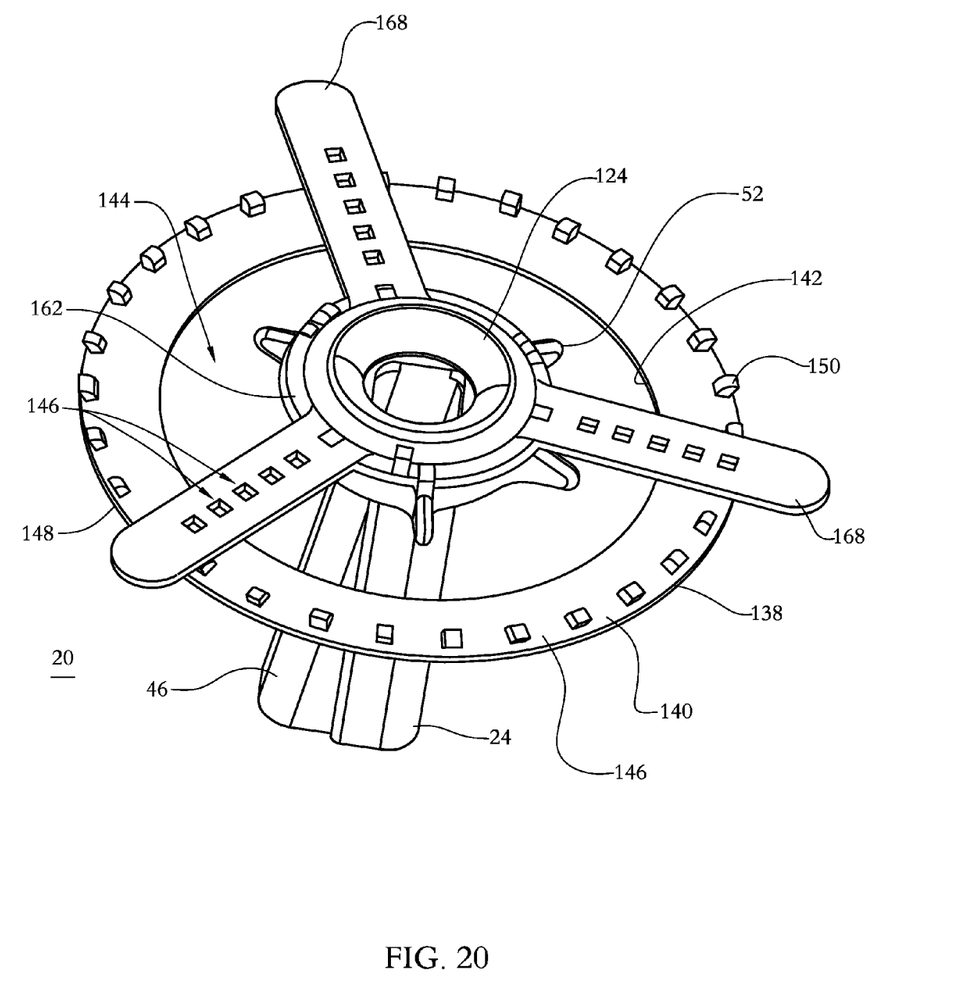
FIG. 20 a perspective view of components of one embodiment of a surgical system in accordance with the principles of the present disclosure.

Cannula 22 comprises a holding member, such as, for example, a fourth member 138 comprising a body 140 including an inner surface 142 defining a pathway 144 configured for disposal of members 24, 46, as will be discussed. Body 140 has an arcuate cross sectional configuration. In some embodiments, body 140 has an oval or racetrack cross sectional configuration, as shown in FIG. 18. In some embodiments, body 140 has a circular cross sectional configuration, as shown in FIG. 20. Surface 146 comprises a first locking element, such as, for example, a projection 150 extending from surface 146. In some embodiments, surface 146 may include one or a plurality of projections 150. Where more than one projection 150 is provided, projections 150 are spaced apart from one another. In some embodiments, projections 150 are positioned radially about body 140 and are evenly spaced apart from one another. In some embodiments, surfaces 146, 148 are each planar. In some embodiments, surface 146 extends parallel to surface 148. In some embodiments, projections 150 extend at an acute angle relative to surface 146, such that projections 150 extend outwardly from an outer surface of body 140 when viewed in a direction that is perpendicular to surface 146, as shown in FIGS. 5 and 6, for example. This configuration provides better engagement between projections 150 and second locking elements, as will be discussed. In some embodiments, projections 150 each include a planar back surface 152 that is aligned with the outer surface of body 140 and a planar front surface 154 opposite surface 152. Projections 150 each include a convexly curved top surface connecting surface 154 with surface 156. In some embodiments, member 138 comprises at least one tab 158 extending from body 140. In some embodiments, member 138 comprises two tabs 158 that are aligned with one another, as shown in FIG. 18, for example. In some embodiments, a lower surface of each tab 158 and/or surface 148 comprises a material, such as, for example, a tacky or sticky material that is able to adhere to the skin of a patient, for example. In some embodiments, an adhesive, such as, for example, a liquid adhesive is applied to lower surface of each tab 158 and/or surface 148. In some embodiments, adhesive tape, such as, for example, double sided tape is adhered to the lower surface of each tab 158 and/or surface 148.

In some embodiments, body 140 and/or pathway 142 may have various cross section configurations, such as, for example, oval, oblong, triangular, rectangular, square, polygonal, irregular, uniform, non-uniform, variable, tubular and/or tapered. In some embodiments, projections 150 may have various surface configurations to enhance fixation with the second locking element, such as, for example, rough, arcuate, undulating, porous, semi-porous, dimpled, polished and/or textured. In some embodiments, projections 150 may be disposed at alternate orientations, relative to surface 146, such as, for example, transverse, perpendicular and/or other angular orientations such as acute or obtuse, co-axial and/or may be offset or staggered. In some embodiments, body 140 comprises a flexible material. In some embodiments, body 140 comprises an elastomeric material. In some embodiments, member 138 is made entirely from molded plastic. In some embodiments, projections 150 are made from a different material than body 140. In some embodiments, projections 150 are made from a material that is less flexible than a material from which body 140 is made. In some embodiments, projections 150 are made from a material that is more rigid than a material from which body 140 is made. In some embodiments, projections 150 are made from the same material body 140 is made from. In some embodiments, projections 150 are flexible relative to body 140 such that projections can be bent without breaking off from body 140. In some embodiments, projections are rigid such that projections cannot be bent without breaking off from body 140.

Cannula 22 includes a fifth member 160 comprising a body 162 including an inner surface 164 configured to engage outer surfaces of fingers 128 between bands 126, 132. In some embodiments, member 160 comprises an elastomeric material, such as, for example, silicone that allows a width or diameter of an opening 1866 of body 162 defined by surface 164 to be stretched for disposal over snap-in ring 124. In some embodiments, a portion of snap-in ring 124 between bands 126, 132 defined by the outer surfaces of fingers 128 has a width or diameter that is slightly less than that of opening 166 and bands 126, 132 have a width or diameter that is greater than that of opening 166. As such, to position the portion of snap-in ring 124 between bands 126, 132 defined by the outer surfaces of fingers 128 within opening 166, opening 166 is enlarged by exerting a force on body 140 to stretch body 140 such that opening 166 has a width or diameter that is larger than that of the portion of snap-in ring 124 between bands 126, 132 defined by the outer surfaces of fingers 128. Body 162 is positioned over snap-in ring 124 such that the portion of snap-in ring 124 between bands 126, 132 defined by the outer surfaces of fingers 128 within opening 166. The force used to stretch body 140 is then removed, allowing opening 166 to return to the unstretched width or diameter such that surface 164 engages the outer surfaces of fingers 128. In some embodiments, member 160 is fixed to snap-in ring 124 when surface 164 engages the outer surfaces of fingers 128. In some embodiments, member 160 is rotatable relative to snap-in ring 124 when surface 164 engages the outer surfaces of fingers 128.

Figure 19:
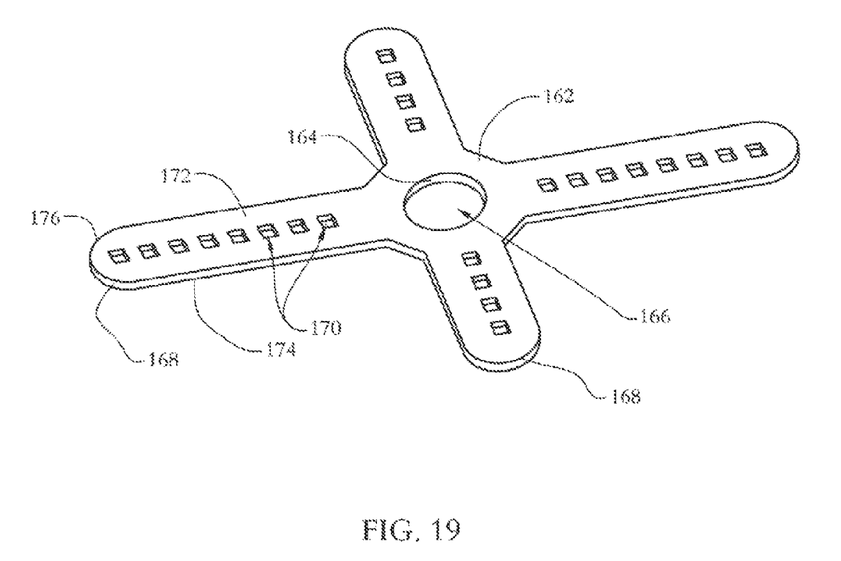
FIG. 19 is a perspective view of a component shown in FIG. 1.

Member 160 comprises a strap 168 extending outwardly from body 162. In some embodiments, member 160 includes one or a plurality of straps 168. In some embodiments, straps 168 are disposed radially about body 162 and are evenly spaced apart from one another. In some embodiments, member 160 includes four straps 168, as shown in FIG. 19. In some embodiments, member 160 includes three straps 168, as shown in FIG. 20. Straps 168 each include a second locking element, such as, for example an aperture 170 extending through a top surface 172 of strap 168 and a bottom surface 174 of strap 168. In some embodiments, straps 168 each include one or a plurality of apertures 168. In some embodiments, straps 168 each include a series of apertures 168 that are positioned in a straight line, as shown in FIG. 19, for example. In some embodiments, apertures 170 each have a polygonal cross sectional configuration. In some embodiments, apertures 170 each have a square cross sectional configuration. In some embodiments, apertures 170 each have a rectangular cross sectional configuration. In some embodiments, surfaces 172, 174 are each planar and extend parallel to one another and apertures 170 each extend perpendicular to surfaces 172, 174. In some embodiments, surfaces 172, 174 are each planar and extend parallel to one another and apertures 170 each extend at an acute angle relative to surfaces 172, 174. In some embodiments, apertures 170 are each angled toward a tip 176 of a respective strap 168 such that straps 168 would need to be pulled in a direction away from opening 166 to remove apertures 170 from projections 156. In some embodiments, apertures 170 may be disposed at alternate orientations, relative to surface 172 and/or surface 172, such as, for example, transverse, perpendicular and/or other angular orientations such as acute or obtuse, co-axial and/or may be offset or staggered. In some embodiments, opening 166 and/or apertures 170 may have various cross section configurations, such as, for example, oval, oblong, triangular, rectangular, square, polygonal, irregular, uniform, non-uniform, variable, tubular and/or tapered. In some embodiments, straps 168 are evenly spaced apart such that on set of adjacent straps 168 are disposed the same angle relative to one another as a second set of adjacent straps 168.

In assembly, operation and use, surgical system 20, similar to that described above, is employed, for example, with a minimally invasive surgical procedure for spinal and neurosurgical applications with a patient. For example, during spine surgery, a surgeon will make an incision in the skin of a patient's back over vertebrae to be treated. One or more dilators may be employed to gradually separate the muscles and create a portal through which the surgery may be performed.

Snap-in ring 124 is positioned relative to body 108 such that extensions 130 are positioned between extension 120 and projection 112. In one embodiment, extensions 130 are positioned between extension 120 and projection 112 by aligning extensions 130 with gaps 122 and translating snap-in ring 124 relative to body 108 in the direction shown by arrow C until extensions 130 are positioned distal to extension 120. Snap-in ring 124 is rotated in a first direction, such as, for example, clockwise or counterclockwise such that extensions 130 are positioned between extension 120 and projection 112 to prevent snap-in ring 124 from moving relative to body 108 in the directions shown by arrows C and D. In one embodiment, fingers 128 are deformable such that snap-in ring 124 is inserted into body 108 by aligning extensions 130 with extensions 120. Snap-in ring 124 is translated relative to body 108 in the direction shown by arrow C until extensions 130 engage extension 120. Snap-in ring 124 is further translated in the direction shown by arrow C such that fingers 128 deflect inwardly to move extensions 130 over extension 120 such extensions 130 are positioned between extension 120 and projection 112 to prevent snap-in ring 124 from moving relative to body 108 in the directions shown by arrow D.

A force is applied to stretch member 160 to increase the width or diameter of opening 166 from a resting or unexpanded width or diameter in which the width or diameter of opening 166 is less than that of band 126 to an expanded width or diameter of opening 166 in which the width or diameter of opening 166 is greater than that of band 126. Member 160 is positioned relative to member 52 with opening having the expanded width or diameter such that opening 166 is positioned about the portion of snap-in ring 124 between bands 126, 132 defined by the outer surfaces of fingers 128. The force used to increase the width or diameter of opening 166 is removed, causing opening 166 to move from the expanded with or diameter to the resting or unexpanded width or diameter such that surface 164 engages the outer surfaces of fingers 128, with body 162 positioned between bands 126, 132. In some embodiments, body 162 has a thickness such that an upper surface of body 162 engages band 126 and a lower surface of body 162 engages band 132 when body 162 positioned between bands 126, 132. In that the resting or unexpanded width or diameter of opening 166 is less than a diameter of bands 126, 132, bands 126, 132 prevent member 160 from moving axially relative to snap-in ring 124 in the direction shown by arrow C or the direction shown by arrow D. Because snap-in ring 124 is fixed with body 108, bands 126, 132 also prevent member 160 from moving axially relative to body 108 in the direction shown by arrow C or the direction shown by arrow D.

In some embodiments, the force used to increase the width or diameter of opening 166 is created by pulling one strap 168 relative to another strap 168. In some embodiments, the force used to increase the width or diameter of opening 166 is created by pulling one strap 168 in a first direction and pulling a another strap 168 that is aligned and/or extends parallel to the one strap 168 in a second direction that is opposite the first direction. In some embodiments, the first direction is a direction that is parallel to the one strap 168.

End 78 is movably positioned in passageway 38 such that outer surfaces of side walls 58 engage portions 56 and surface 94 engages surface 60. Member 46 is translated relative to member 24 in the direction shown by arrow C. As member 46 translates relative to member 24 in the direction shown by arrow C, the outer surfaces of side walls 58 slide along portions 56 and surface 94 slides along surface 60. Member 46 is translated in the direction shown by arrow C until protrusions 44 are disposed in recesses 42 to provisionally fix member 46 relative to member 24. When protrusions 44 are disposed in recesses 42, lip 80 engages flange 30 and member 46 extends parallel to axis A.

Figure 1:
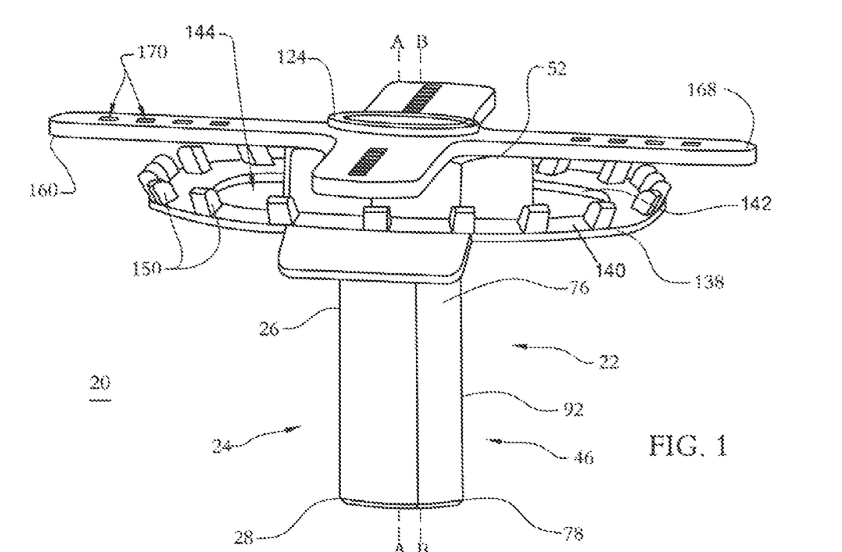
FIG. 1 is a perspective view of components of one embodiment of a surgical system in accordance with the principles of the present disclosure.
Figure 2:
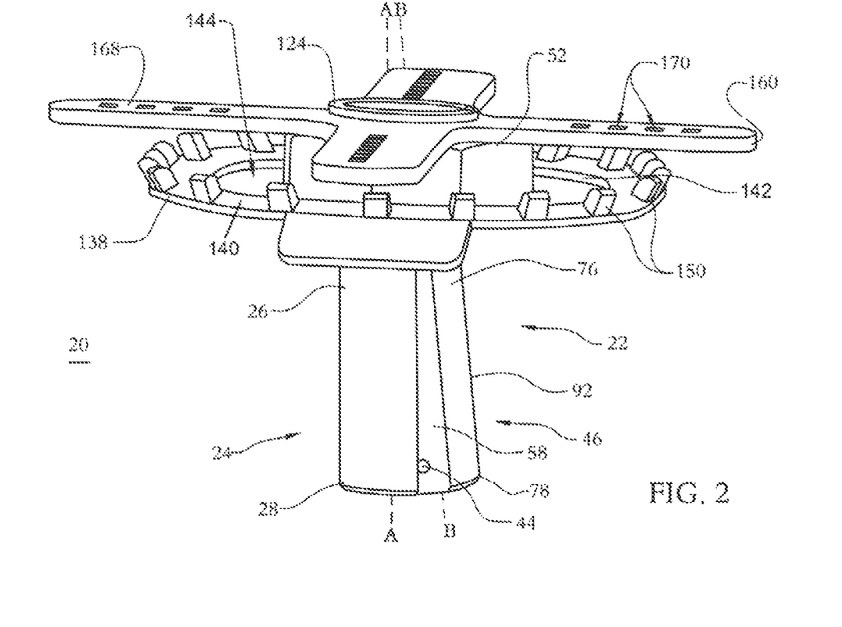
FIG. 2 is a perspective view of components shown in FIG. 1.

Member 52 is positioned relative to member 24 with member 52 in a first configuration, shown in FIGS. 1, 3 and 5, such that thread form 50 is aligned with thread form 48 and surface 114 is spaced apart from surface 88 and/or surface 88 does not apply force upon surface 114 sufficient to move lip 80 such that lip 80 is parallel with flange 30. When member 52 is in the first configuration, protrusions 44 are disposed in recesses 42, which provisionally fix member 46 relative to member 24, as discussed above. Member 52 is rotated about axis A to move member 52 from the first configuration to a second configuration in which surface 114 engages surface 88 to apply a force upon lip 80 sufficient to move lip 80 such that surface 90 engages flange 30 and lip 80 extends parallel to flange 30. When member 52 is in the second configuration, member 46 extends at an acute angle relative to axis A, as shown in FIGS. 2, 4 and 6. In some embodiments, the acute angle is equal to angle 82.

As member 52 is rotated about axis A, member 52 translates axially in the direction shown by arrow C. As member 52 moves in the direction shown by arrow C, surface 114 applies a force upon surface 88 causing surface 90 to engage lip 30 such that lip 80 extends parallel to flange 30. As surface 114 applies a force upon surface 88, member 46 deflects outwardly from member 24, as shown in FIGS. 2, 4 and 6. Member 52 is rotated about axis A until surface 114 exerts a force upon surface 88 that is sufficient to cause member 46 to deflect outwardly from member 24 such that protrusions 44 disengage recesses 42 such that protrusions 44 are spaced apart from recesses 42. Due to the transverse orientation of lip 80, the force causes member 46 to deflect outwardly away from axis A as surface 114 exerts a force on lip 80 such that member 46 extends at an acute angle relative to axis A, as shown in FIGS. 2, 4 and 6. When member 46 extends at an acute angle relative to axis A, member 52 is in the second configuration.

Member 138 is affixed to the skin of the patient. In some embodiments, an adhesive is applied to surface 148 and/or the lower surface of at least one of tabs 158 before affixing member 138 to the skin of the patient. In some embodiments, at least one strip of tape is applied to surface 148 and/or the lower surface of at least one of tabs 158 before affixing member 138 to the skin of the patient. The assembly of members 24, 46, 52 and 160 is positioned relative to member 138 such that at least members 24, 46 are positioned in pathway 142 with member 52 in the first configuration. Once the assembly of members 24, 46, 52 and 160 is selectively positioned in pathway 142, member 160 is positioned relative to member 138 such that at least one of projections 150 is aligned with at least one of apertures 170. Member 160 is manipulated relative to member 138 such that projection(s) 150 is/are disposed in aperture(s) 170 to fix the assembly of members 24, 46, 52 and 160 relative to member 138. In some embodiments, member 160 is positioned relative to member 138 such that at least one aperture 170 of each strap 168 is aligned with one of projections 150 and member 160 is manipulated relative to member 138 such that the projections 150 are disposed in the apertures 170 to fix the assembly of members 24, 46, 52 and 160 relative to member 138. In some embodiments, member 160 is fixed to snap-in ring 124 and positioning member 160 relative to member 138 comprises rotating member 160 relative to snap-in ring 124. In some embodiments, member 160 is rotatable relative to snap-in ring 124 and positioning member 160 relative to member 138 comprises rotating snap-in ring 124 relative to body 108.

Member 52 is moved from the first configuration, shown in FIGS. 1, 3 and 5, to the second configuration, shown in FIGS. 2, 4 and 6. When member 52 in the second configuration, outer surfaces of members 24, 46 engage tissue, such as, for example, soft tissue, ligaments, tendons, cartilage and/or bone. Members 24, 46 space apart tissue and create access and/or a surgical pathway to a surgical site. That is, when member 52 in the second configuration, an item, such as, for example, a surgical instrument may be inserted through a passage defined by passageway 38 and conduit 96 and/or a surgical procedure may be performed within the passage. In some embodiments, member 52 is moved from the first configuration to the second configuration after projection(s) 150 is/are disposed in the aperture(s) 170. In some embodiments, member 52 is moved from the first configuration to the second configuration after projection(s) 150 is/are disposed in the aperture(s) 170.

In some embodiments, after the surgical procedure is performed and/or the surgical instrument is inserted through the passage, member 52 is moved from the second configuration to the first configuration by rotating member 52 relative to member 24 about axis A such that member 52 moves in the direction shown by arrow D. Member 160 is manipulated relative to member 138 such that projection(s) 150 is/are removed from aperture(s) 170 such that the assembly of members 24, 46, 52 and 160 is movable relative to member 138. The assembly of members 24, 46, 52 and 160 is positioned relative to member 138 such that at least members 24, 46 are positioned in pathway 142 with member 52 in the first configuration. Once the assembly of members 24, 46, 52 and 160 is selectively positioned in pathway 142, member 160 is positioned relative to member 138 such that at least one of projections 150 is aligned with at least one of apertures 170. Member 160 is manipulated relative to member 138 such that projection(s) 150 is/are disposed in aperture(s) 170 to fix the assembly of members 24, 46, 52 and 160 relative to member 138. In some embodiments, member 160 is positioned relative to member 138 such that at least one aperture 170 of each strap 168 is aligned with one of projections 150 and member 160 is manipulated relative to member 138 such that the projections 150 are disposed in the apertures 170 to fix the assembly of members 24, 46, 52 and 160 relative to member 138. Member 52 is moved from the first configuration, shown in FIGS. 1, 3 and 5, to the second configuration, shown in FIGS. 2, 4 and 6. When member 52 in the second configuration, outer surfaces of members 24, 46 engage tissue, such as, for example, soft tissue, ligaments, tendons, cartilage and/or bone. Members 24, 46 space apart tissue and create access and/or a surgical pathway to a surgical site. That is, when member 52 in the second configuration, an item, such as, for example, a surgical instrument may be inserted through a passage defined by passageway 38 and conduit 96 and/or a second surgical procedure may be performed within the passage. In some embodiments, after the second surgical procedure is performed and/or the surgical instrument is inserted through the passage, member 52 is moved from the second configuration to the first configuration. Member 160 is manipulated relative to member 138 such that projection(s) 150 is/are removed from aperture(s) 170 such that the assembly of members 24, 46, 52 and 160 is movable relative to member 138. The assembly of members 24, 46, 52 and 160 is removed from the patient. In some embodiments, member 138 may be removed from the patient.

In some embodiments, at least one of light sources 72, 104 are in an on position as member 52 moves from the first configuration to the second configuration. In some embodiments, at least one of light sources 72, 104 are moved from an off position to an on position after member 52 is moved from the first configuration to the second configuration. When light sources 72, 104 are in an on position, light sources 72, 104 emit light into the passage defined by passageway 38 and conduit 96 to aid in visualization to perform a surgical procedure, for example. In some embodiments, light sources 72, 104 are configured to emit light without creating shadows, making cannula 22 useful for imaging purposes, for example. Upon completion of the surgical procedure, cannula 22 is removed from the surgical site.

It is envisioned that the use of microsurgical and image guided technologies may be employed to access, view and repair spinal deterioration or damage, with the aid of cannula 22. It is contemplated that a surgical procedure may employ other instruments that can be mounted with cannula 22, such as, for example, nerve root retractors, tissue retractors, forceps, cutter, drills, scrapers, reamers, separators, rongeurs, taps, cauterization instruments, irrigation and/or aspiration instruments, illumination instruments and/or inserter instruments.

Cannula 22 may be employed for performing spinal surgeries, such as, for example, laminectomy, discectomy, fusion, laminotomy, nerve root retraction, foramenotomy, facetectomy, decompression, spinal nucleus or disc replacement and procedures using bone graft and implantable prosthetics including plates, rods, and bone engaging fasteners.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument, comprising:
a first member extending along a first longitudinal axis between opposite first and second ends, the first end including a flange extending transverse to the first longitudinal axis;
a second member extending along a second longitudinal axis between opposite first and second ends, the first end of the second member comprising a lip that engages the flange, the lip extending transverse to the second longitudinal axis; and
a third member comprising an end surface configured to engage the lip,
wherein the third member is movable relative to the first and second members between a first configuration in which the end surface is spaced apart from the lip and the second longitudinal axis extends parallel to the first longitudinal axis and a second configuration in which the end surface engages the lip and the second longitudinal axis extends at an acute angle relative to the first longitudinal axis,
wherein an inner surface of the third member comprises an internal thread form and an outer surface of the first member comprises an external thread form that engages the internal thread form to move the third member between the first and second configurations; and
wherein the end surface is positioned between the internal thread form and an upper surface of the third member.

2. A surgical instrument as recited in claim 1, wherein the lip extends at an acute angle relative to the first longitudinal axis when the third member is in the first configuration and the lip extends parallel to the first longitudinal axis when the third member is in the second configuration.

3. A surgical instrument as recited in claim 1, wherein the third member moves between the first and second configurations by rotating the third member relative to the first and second members.

4. A surgical instrument as recited in claim 1, wherein:
an inner surface of the first member comprises a recess and an outer surface of the second member comprises a projection; and
the projection is disposed in the recess when the third member is in the first configuration and is spaced apart from the recess when the third member is in the second configuration.

5. A surgical instrument as recited in claim 4, wherein the recess and the projection each have a hemispherical configuration.

6. A surgical instrument as recited in claim 1, wherein at least one of the first member and the second member comprises a light source.

7. A surgical instrument as recited in claim 6, wherein the light source is a light emitting diode.

8. A surgical instrument as recited in claim 1, wherein:
the flange comprises an arcuate portion extending between linear portions of the flange, the first member comprising an arcuate surface opposite the arcuate portion;
the second member comprises a wall including an arcuate outer surface that extends between planar side walls of the second member; and
the arcuate outer surface slidingly engages the arcuate surface and the side walls slidingly engage the linear portions.

* * * * *

UNITED STATES PATENT AND TRADEMARK OFFICE
CERTIFICATE OF CORRECTION

PATENT NO.        : 9,675,333 B2                                          Page 1 of 1
APPLICATION NO.   : 14/309604
DATED             : June 13, 2017
INVENTOR(S)       : Lauchner et al.

It is certified that error appears in the above-identified patent and that said Letters Patent is hereby corrected as shown below:

In the Drawings

In Fig. 2, Sheet 1 of 8, delete " " and insert --                                            --, therefor.

In the Specification

In Column 4, Line 1, delete "am" and insert -- are --, therefor.

In Column 6, Line 36, delete "tight" and insert -- light --, therefor.

In Column 7, Line 14, delete "8," and insert -- B, --, therefor.

In Column 10, Line 26, delete "1866" and insert -- 166 --, therefor.

Signed and Sealed this
Fifth Day of September, 2017

Joseph Matal
*Performing the Functions and Duties of the
Under Secretary of Commerce for Intellectual Property and
Director of the United States Patent and Trademark Office*